United States Patent
Sun et al.

(10) Patent No.: US 9,816,176 B2
(45) Date of Patent: Nov. 14, 2017

(54) PREPARATION METHOD FOR MULTI-LAYER METAL OXIDE POROUS FILM NANO GAS-SENSITIVE MATERIAL

(71) Applicant: SOOCHOW UNIVERSITY, Suzhou (CN)

(72) Inventors: Xuhui Sun, Suzhou (CN); Pingping Zhang, Suzhou (CN); Shumin Zhang, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 34 days.

(21) Appl. No.: 15/030,893

(22) PCT Filed: Apr. 8, 2014

(86) PCT No.: PCT/CN2014/074881
§ 371 (c)(1),
(2) Date: Sep. 2, 2016

(87) PCT Pub. No.: WO2015/058495
PCT Pub. Date: Apr. 30, 2015

(65) Prior Publication Data
US 2017/0152595 A1    Jun. 1, 2017

(30) Foreign Application Priority Data
Oct. 21, 2013    (CN) .......................... 2013 1 0491742

(51) Int. Cl.
*B31D 3/00*     (2017.01)
*B44C 1/22*     (2006.01)
(Continued)

(52) U.S. Cl.
CPC .......... *C23C 14/352* (2013.01); *C23C 14/086* (2013.01); *C23C 14/087* (2013.01); *G01N 27/127* (2013.01)

(58) Field of Classification Search
None
See application file for complete search history.

(56) References Cited

U.S. PATENT DOCUMENTS 5,801,092 A      9/1998  Ayers
2005/0224779 A1* 10/2005 Wang ............... B82Y 10/00
                                                    257/9

(Continued)

FOREIGN PATENT DOCUMENTS

CN    2124473 U    12/1992
CN    1391097 A     1/2003

(Continued)

*Primary Examiner* — Shamim Ahmed
(74) *Attorney, Agent, or Firm* — Gokalp Bayramoglu (57) ABSTRACT

The present invention discloses a method for preparing a multilayer metal oxide nano-porous thin film gas sensitive material, in which the microsphere aqueous solution is self-assembled on a substrate covered with an insulating layer, to form a compact single-layer array template; the surface of these microspheres are etched by using a plasma etching method to reduce the pitches between the microspheres; the metal oxide thin film is deposited by a physical deposition method; the template is removed by ultrasonic treatment with a solvent to prepare a porous array metal oxide thin film; and annealing is performed in air atmosphere to obtain the metal oxide porous thin film gas sensitive material. The present invention can be used for preparing a regular porous array thin film gas sensitive material; the pore size of the prepared porous thin film material is uniform and controllable; and the combination of these materials is controllable.

4 Claims, 8 Drawing Sheets (51) Int. Cl.
    *C23C 14/35*     (2006.01)
    *G01N 27/12*     (2006.01)
    *C23C 14/08*     (2006.01)

(56) References Cited

U.S. PATENT DOCUMENTS

2009/0269558 A1*  10/2009  Himmelhaus ......... C23C 14/042
                                                                   428/195.1
2016/0231435 A1*  8/2016  Alvine .................. C23C 14/024

FOREIGN PATENT DOCUMENTS

| CN | 1967230 A | | 5/2007 |
|---|---|---|---|
| CN | 102633230 A | * | 8/2012 |
| CN | 103529081 A | | 1/2014 |

\* cited by examiner

PREPARATION METHOD FOR MULTI-LAYER METAL OXIDE POROUS FILM NANO GAS-SENSITIVE MATERIAL

BACKGROUND OF THE INVENTION

Field of the Invention

The present invention relates to the field of gas sensitive materials for gas sensors, and in particular, to a method for preparing a multilayer metal oxide nano-porous thin film gas sensitive material.

Description of Related Art

With rise of the living standards, toxic and harmful gases are everywhere in our lives, and greatly harm the health of the people. Therefore, it is a rather difficult task for researchers to develop a toxic gas sensor of high performance (high sensitivity, high selectivity, and good stability). Metal oxides, as mature gas sensitive materials, are increasingly used by the researchers due to advantages of low cost, stable performance, and capability of performing sensitive detection of low detection limits for various types of gases. The gas sensitive performance of a gas sensitive material is greatly related to the specific surface area of the material. A larger specific surface area of the material leads to more reaction sites in contact with the gas and higher reaction sensitivity to some extent. Therefore, it is a trend of modern researches on the gas sensitive material to make the metal oxide smaller in size to increase its specific surface area, thereby enhancing the response of the gas sensitive material.

The metal oxide porous film material, as a good, gas sensitive material, has higher sensitivity to gas because its specific surface area is larger than that of a bulk film material. In recent years, making the metal oxide film into a porous structure so as to enhance the gas sensitive response of the gas sensitive material is gradually becoming a trend, and also gets more attention from the researchers.

An ordered porous array film material has a high specific surface area as well as a perfect and regular porous array structure, and thus can be well applied in a gas sensitive sensor, such that its application in gas sensors is also becoming a trend. In terms of detection of polluting gases, it is expected and also a challenge to use a metal oxide nano-porous material as a gas sensitive material to improve the selectivity, repeatability and stability of gas sensors. However, the above perfect strategy requires that a perfect nano-porous structure material is synthesized first, and thus the synthesis of the nano-porous material has become a critical factor for wide application of the nano-porous material in high-efficiency gas sensitive devices. At present, some metal oxide porous materials have been prepared by a hydrothermal method, a template preparation method and so on, and a metal oxide porous material, a metal-doped metal oxide porous material, and a mixed metal oxide porous material have also been reported successively. According to the mutual enhancement theory of multiple types of gas sensitive materials, the mutual assisting effect of two different types of metal oxides enables that the gas sensitive response of a combination of two different types of metal oxide gas sensitive materials is higher than the gas sensitive response of a single gas sensitive material, and the gas sensitive parameters are improved. Therefore, the preparation of a multilayer porous film of two or more different types of materials has gradually become a focus in the research on the gas sensitive material, and has a great application prospect in the field of gas sensitive sensors in the future.

SUMMARY OF THE INVENTION

Technical Problem

The objective of the present invention is to overcome the above problems in the prior art, and to provide a method for preparing a multilayer metal oxide nano-porous film gas sensitive material, so as to prepare a regular porous array film gas sensitive material and improve the gas sensitive performance of the material through the combination of different materials.

Technical Solution

In order to achieve the above technical objective and the above technical effects, the present invention is implemented through the following technical solution:

A method for preparing a multilayer metal oxide nano-porous film gas sensitive material includes the following steps:

Step 1) self-assembling the microsphere template on a substrate covered with an insulating layer by means of an LB membrane method, a solution evaporation method, a spin-coating method or a dip-coating method, to form a compact single-layer array template;

Step 2) reducing the pitches between microspheres by etching, the pitch being in the range of 1 nm to 1 µm;

Step 3) depositing a metal oxide film by means of physical deposition; and

Step 4) removing the template to prepare a porous array metal oxide film, and performing annealing to obtain a metal oxide porous film gas sensitive material.

Further, the insulating layer in Step 1 is preferably made of $SiO_x$, where $1 \leq x \leq 2$, the thickness of the insulating layer is between 100 nm and 10 µm, and the substrate is one selected from Si, SiC, $Si_3N_4$, and ceramics substrates, preferably a Si substrate made of $SiO_2$.

Further, the microsphere template in Step 1 is a polystyrene microsphere aqueous solution or a silicon dioxide microsphere aqueous solution, preferably the polystyrene microsphere aqueous solution; the volume-mass concentration of the polystyrene microsphere aqueous solution is 0.5% to 3% mg/ml, preferably 1% mg/ml; and the diameter of the microsphere template is 100 nm to 5 µm, preferably 500 nm.

Further, the etching method in Step 2 includes plasma dry etching or HF solution wet etching; when the microsphere template is the polystyrene microsphere aqueous solution, plasma dry etching is selected, and when the microsphere template is the silicon dioxide microsphere aqueous solution, HF solution wet etching or plasma dry etching is selected; and the plasma in plasma dry etching, comes from a plasma etching machine or a reactive ion etching machine.

Further, the physical deposition in Step 3 is magnetron sputter physical deposition or electron beam evaporation physical deposition.

Further, when the microsphere template is the polystyrene microsphere aqueous solution, an organic solvent is selected to perform ultrasonic treatment so as to remove the template, and when the microsphere template is the silicon dioxide microsphere aqueous solution, an HF solution is selected to perform ultrasonic treatment. The annealing temperature in Step 4 is 200° C. to 1000° C., and the annealing time is 0.5 h to 10 h.

The gas sensitive response of the metal oxide porous film gas sensitive material prepared by the method of the present invention depends on the combination manners of the materials and the diameter of pores in the porous film. The diameter of the pores depends on the characteristic of the plasma etching time. For example, after PS spheres with the diameter of 500 nm are etched for 1 min by using $O_2$ plasma excitation power of 90 W, the diameter of the PS becomes 450 nm, and after the PS spheres are etched for 2 min, the diameter of the PS microspheres becomes 400 nm. When the porous film is made of a single type of a metal oxide, the larger pore size of the porous film leads to higher gas sensitive response. When the diameter of the pores of the porous film is equal to the thickness of the film, the gas sensitive response of the prepared porous film made of two layers of different types of metal oxides is higher than that of the porous film made of a single type of a metal oxide, and the gas sensitive response of the prepared porous film made of three layers of different types of metal oxides is higher than that of the porous film made of two layers of metal oxides.

Advantageous Effect

The present invention has the following beneficial effects:
A high quality single-layer or multilayer metal oxide porous film gas sensitive material can be prepared by means of the present invention, and the prepared metal oxide porous film gas sensitive material has good integrity, a uniform diameter of the porous structure, and superior gas sensitive performance.

DETAILED DESCRIPTION OF THE INVENTION

The present invention is illustrated in detail below with reference to the embodiments and the accompanying drawings.

A method for preparing a multilayer metal oxide nanoporous film gas sensitive material includes the following steps:

Step 1) self-assembling a microsphere template on a substrate covered kith an insulating layer by means of an LB membrane method, a solution evaporation method, a spin-coating method or a dip-coating method, to form a compact single-layer array template;

Step 2) reducing the pitches between microspheres by etching, the pitch being in the range of 1 nm to 1 μm;

Step 3) depositing a metal oxide film by means of physical deposition; and

Step 4) removing the template to prepare a porous array metal oxide film, and performing annealing to obtain a metal oxide porous film gas sensitive material.

Further, the insulating layer in Step 1 is preferably made of $SiO_x$, where $1 \leq x \leq 2$, the thickness of the insulating layer is between 100 nm and 10 μm, and the substrate is one selected from Si, SiC, $Si_3N_4$, and ceramics substrates, preferably a Si substrate made of $SiO_2$.

Further, the microsphere template in Step 1 is a polystyrene microsphere aqueous solution or a silicon dioxide microsphere aqueous solution, preferably the polystyrene microsphere aqueous solution; the volume-mass concentration of the polystyrene microsphere aqueous solution is 0.5% to 3% mg/ml, preferably 1% mg/ml; and the diameter of the microsphere template is 100 nm to 5 μm, preferably 500 nm.

Further, the etching method in Step 2 includes plasma dry etching or HF solution wet etching; when the microsphere template is the polystyrene microsphere aqueous solution, plasma dry etching is selected, and when the microsphere template is the silicon dioxide microsphere aqueous solution, HF solution wet etching or plasma dry etching is selected; and the plasma in plasma dry etching comes from a plasma etching machine or a reactive ion etching machine.

Further, the, physical deposition in Step 3 is magnetron sputter physical deposition or electron beam evaporation physical deposition.

Further, when the microsphere template is the polystyrene microsphere aqueous solution, an organic solvent is selected to perform ultrasonic treatment so as to remove the template, and when the microsphere template is the silicon dioxide microsphere aqueous solution, an HF solution is selected to perform ultrasonic treatment. The annealing temperature in Step 4 is 200° C. to 1000° C., and the annealing time is 0.5 h to 10 h.

EXAMPLE 1

Figure 1:
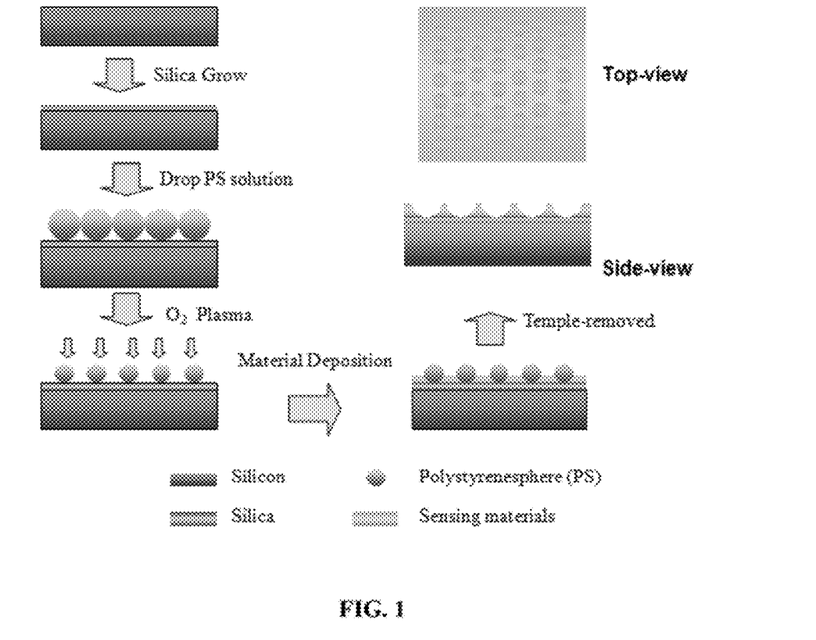
FIG. 1 is a schematic diagram of steps for preparing a single-layer metal oxide porous film gas sensitive material.
Figure 2:
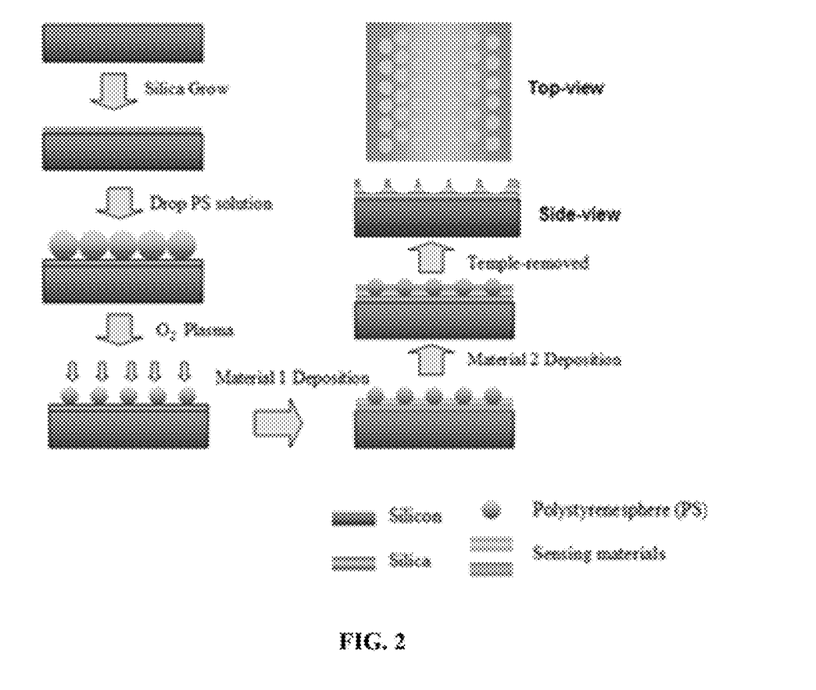
FIG. 2 is a schematic diagram of steps for preparing a double-layer and multilayer metal oxide porous film gas sensitive materials.
Figure 3:
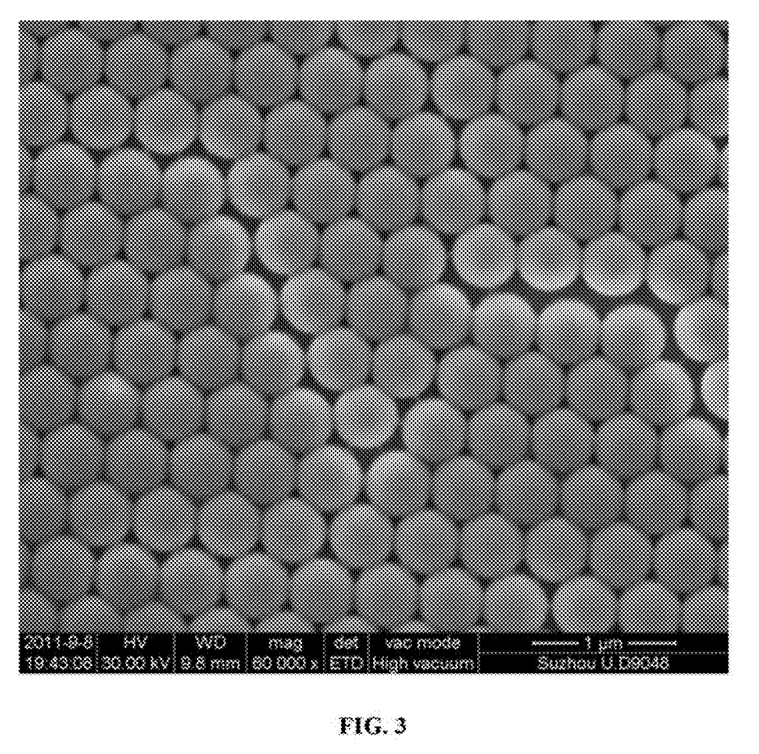
FIG. 3 is a morphology from a scanning electron microscope (SEM) after polystyrene microspheres are self-assembled into a single-layer film in Example 1.
Figure 4:
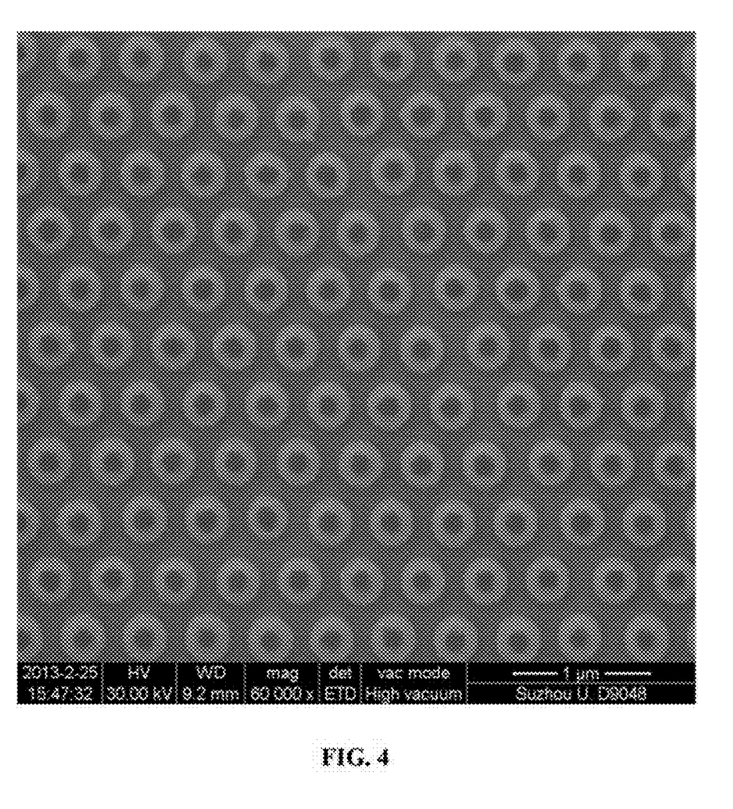
FIG. 4 is a morphology from the SEM after plasma etching is performed on the polystyrene microspheres in Example 1.
Figure 5:
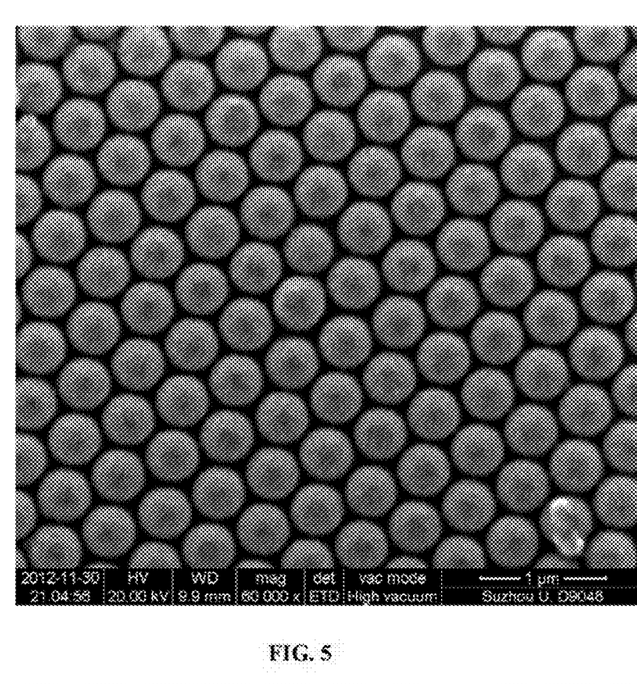
FIG. 5 is a morphology from the SEM after the polystyrene microspheres are etched and then metal oxide films are sequentially deposited in Example 1.
Figure 6:
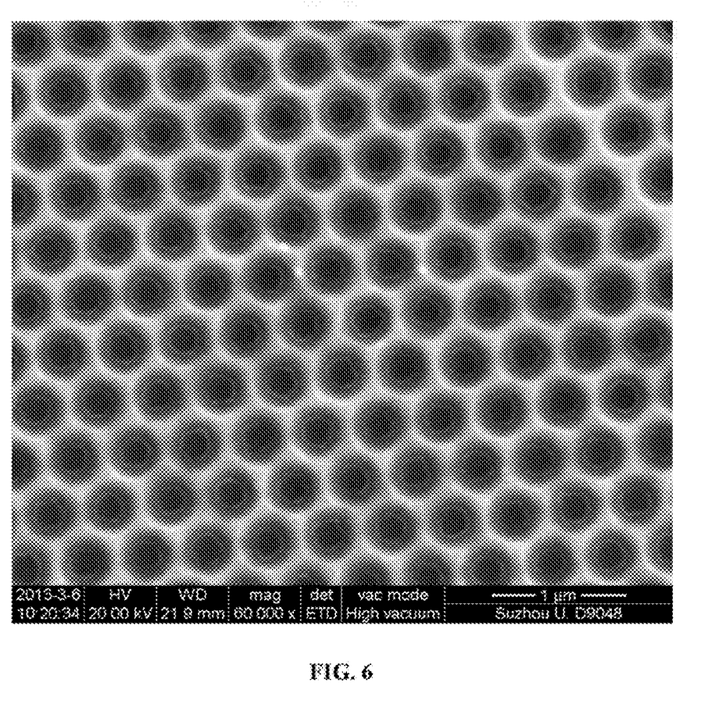
FIG. 6 is a morphology from the SEM of a double-layer metal oxide porous film prepared after removal of the template and then annealing in Example 1.
Figure 7:
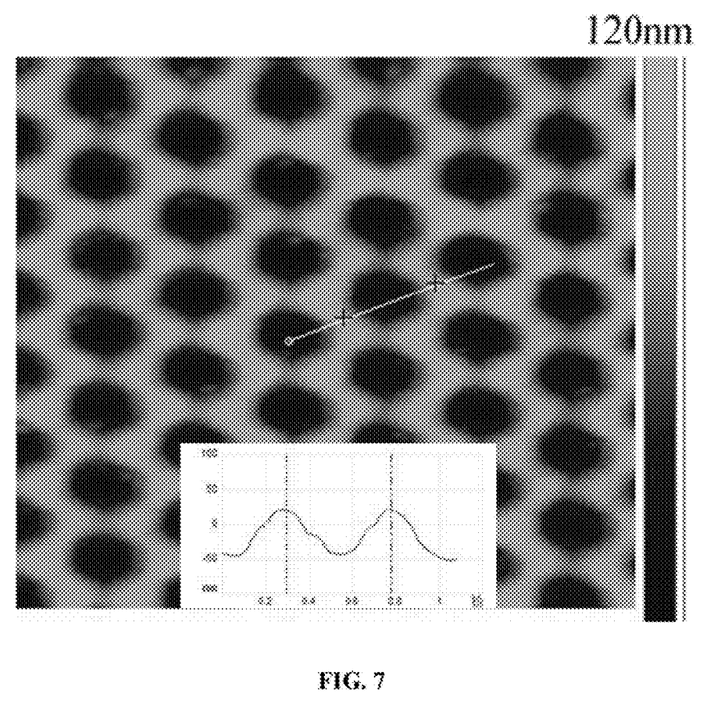
FIG. 7 is a 2D morphology from an atomic force microscope (AFM) of the double-layer metal oxide porous film prepared in Example 1.

FIG. 1 is a diagram of steps for preparing a single-layer metal oxide porous film, FIG. 2 is a schematic diagram of steps for preparing a double-layer metal oxide porous film, and in the figures, the substrate of the obtained metal oxide porous film is a silicon wafer substrate covered with a monocrystal $SiO_2$ oxide layer with a thickness of 150 nm.

The used PS microsphere template is a non-functional PS aqueous solution having a diameter of 500 nm, and the mass-volume concentration of the aqueous solution is 1% mg/ml. The polystyrene microsphere single-layer template was self-assembled on a Si substrate covered with $SiO_2$ by using a solution evaporation method, the PS template was etched by using a reactive ion etching method so as to reduce the pitches between PS, and in the process of using a reactive ion etching machine, the flow rate of the fed $O_2$ was controlled to be 40 sccm, the pressure in the cavity was controlled to be 37 mTorr, the power applied to excite the $O_2$ plasma was controlled to be 90 W, and the $O_2$ plasma etching time was controlled to be 1 min. A magnetron sputter physical deposition method was used to deposit, on four processed substrates, 80 nm ZnO, 80 nm $TiO_2$, 40 nm ZnO+40 nm $TiO_2$ (with titanium oxide being in the bottom layer, and zinc oxide being in the top layer), and 40 nm $TiO_2$+40 nm ZnO (with zinc oxide being in the bottom layer, and titanium oxide being in the top layer) respectively. In the process of depositing a metal oxide film by means of magnetron sputter physical deposition, the power for exciting the Ar plasma was 80 W, and the pressure in the cavity was 3 mTorr. A sample was placed in toluene for ultrasonic treatment for 2 min to remove the PS template, and annealing was performed for 4 h in air atmosphere at the temperature of 550° C. The target materials used in magnetron sputter were respectively ceramics target materials of titanium oxide and zinc oxide.

Figure 8:
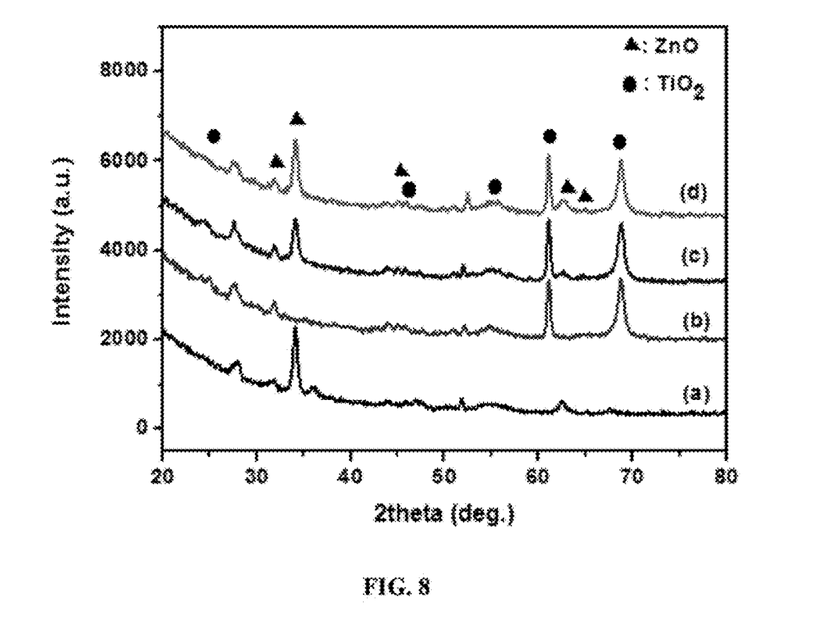
FIG. 8 is an X-ray diffraction (XRD) spectrum of different metal oxide porous films prepared in Example 1.
Figure 9:
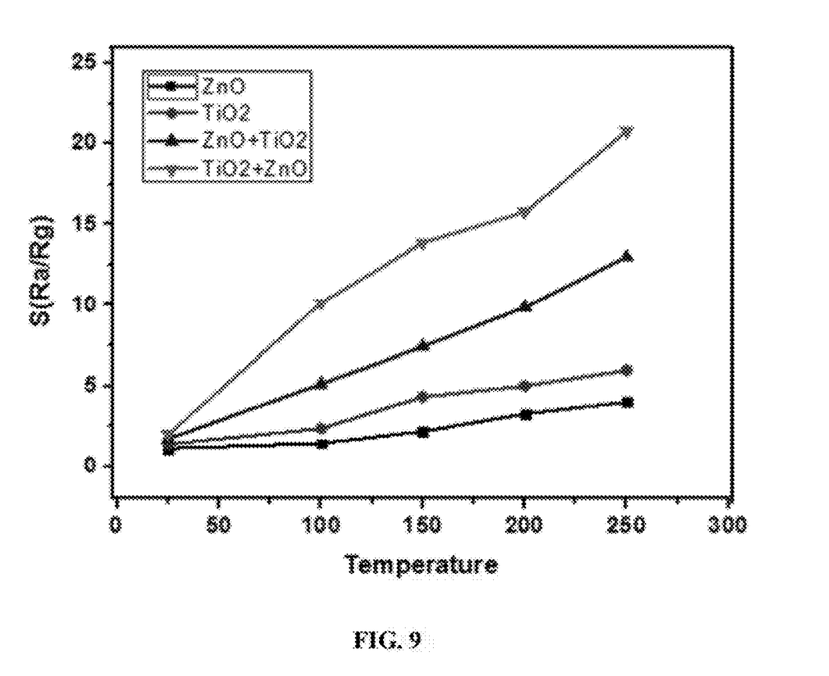
FIG. 9 is a comparison diagram of sensitivity curves of different metal oxide porous films prepared in Example 1 with respect to ethanol of 1000 ppm at different temperatures.
Figure 10:
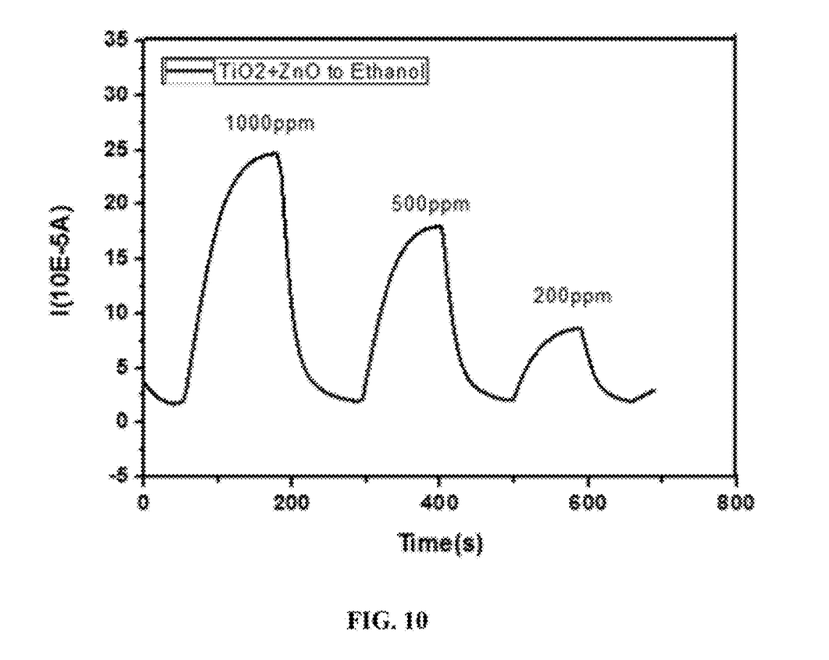
FIG. 10 is a diagram of a sensitivity curve of a multilayer metal oxide porous film prepared in Example 1 of the present invention with respect to ethanol of different concentrations at the temperature of 150° C.
Figure 11:
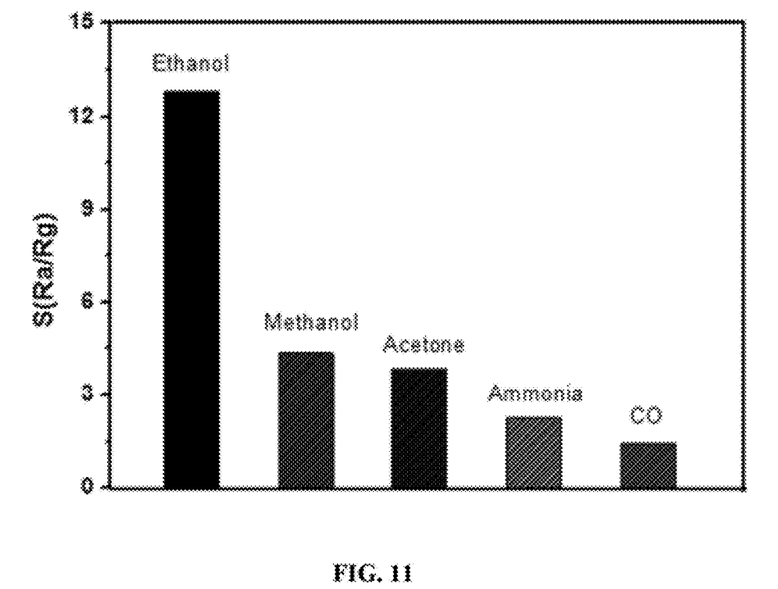
FIG. 11 is a diagram of selectivity of the multilayer metal oxide porous film prepared in Example 1 with respect to ethanol of 1000 ppm at the temperature of 150° C.

The morphology after self-assembly of the PS template, the morphology of the PSs after processing of the plasma, the morphology after deposition of the metal oxide, and the morphology of the porous film after removal of the PS template that are obtained in the process of preparing the metal oxide porous film gas sensitive material by using this method are shown in FIGS. 3, 4, 5, 6, and 7, and it can be seen from these figures that, the diameter of the pores in the prepared metal oxide porous film is quite uniform and is around 450 nm. The X-ray film diffraction of various types of metal oxide porous film gas sensitive materials prepared by using this method is shown in FIG. 8, and it can be seen from the figure that, the prepared metal oxide porous film has a good crystal form. The diagrams of the gas sensitive responses of the metal oxide porous film gas sensitive material prepared by using this method with respect to ethanol at different temperatures, the gas sensitive responses of the double-layer metal oxide porous film with respect to ethanol of different concentrations, and the selectivity of the double-layer metal oxide porous film with respect to ethanol of a certain concentration at a certain temperature are shown in FIGS. 9, 10, and 11. It can be seen from FIG. 9 that, the gas sensitive response of the prepared single-layer metal oxide porous film is lower than the gas sensitive response of the double-layer metal oxide porous film, and it can also be seen that the gas sensitive response of the material is improved with the increase of the temperature within a certain temperature range, the gas sensitive responses of the three metal oxide porous films all satisfy the above condition, and the higher the temperature within the temperature range is, the higher the gas sensitive responses of the metal oxide porous films are. It can be seen from FIG. 10 that, the gas sensitive response of the, prepared metal oxide porous film is improved with the increase of the gas concentration. It can be seen from FIG. 11 that, the prepared double-layer metal oxide porous film has a preferable selectivity to ethanol.

EXAMPLE 2

In the schematic diagram of steps for preparing a multilayer metal oxide porous film shown in FIG. 2, the substrate of the obtained metal oxide porous film is a silicon wafer substrate covered with a monocrystal $SiO_2$ oxide layer having a thickness of 150 nm. The used PS microsphere template is a non-functional polystyrene sphere (PS) aqueous solution having a diameter of 500 nm, and the mass-volume concentration of the aqueous solution is 1% mg/ml. The polystyrene microsphere single-layer template was self-assembled on a Si substrate covered with $SiO_2$ by using a solution evaporation method, the PS template was etched by using a reactive ion etching method so as to reduce the pitches between PS, and the flow rate of the fed $O_2$ was controlled to be 40 sccm, the pressure in the cavity was controlled to be 37 mTorr, the power applied to excite the $O_2$ plasma was controlled to be 90 W, and the $O_2$ plasma etching time was controlled to be 1 min. A magnetron sputtering physical deposition method was used to deposit, on four processed substrates, 40 nm $Cu_2O$+40 nm $In_2O_3$ (with indium oxide being in the bottom layer, and cuprous oxide being in the top layer), 40 nm $In_2O_3$+40 nm $Cu_2O$ (with cuprous oxide being in the bottom and indium oxide being in the top layer), 30 nm $Cu_2O$+20 nm $In_2O_3$+30 nm $Cu_2O$ (with indium oxide being in the intermediate layer) and 30 nm $In_2O_3$+20 nm $Cu_2O$+30 nm $In_2O_3$ (with cuprous oxide being in the intermediate layer) respectively. The target materials used for magnetron sputter were respectively ceramics target materials of indium oxide and cuprous oxide, h power for exciting the Ar plasma was 80 W, and the pressure in the cavity was 3 mTorr. A sample was placed in toluene for ultrasonic treatment to remove the PS template, and annealing was performed for 4 h in air atmosphere at the temperature of 550° C.

Figure 12:
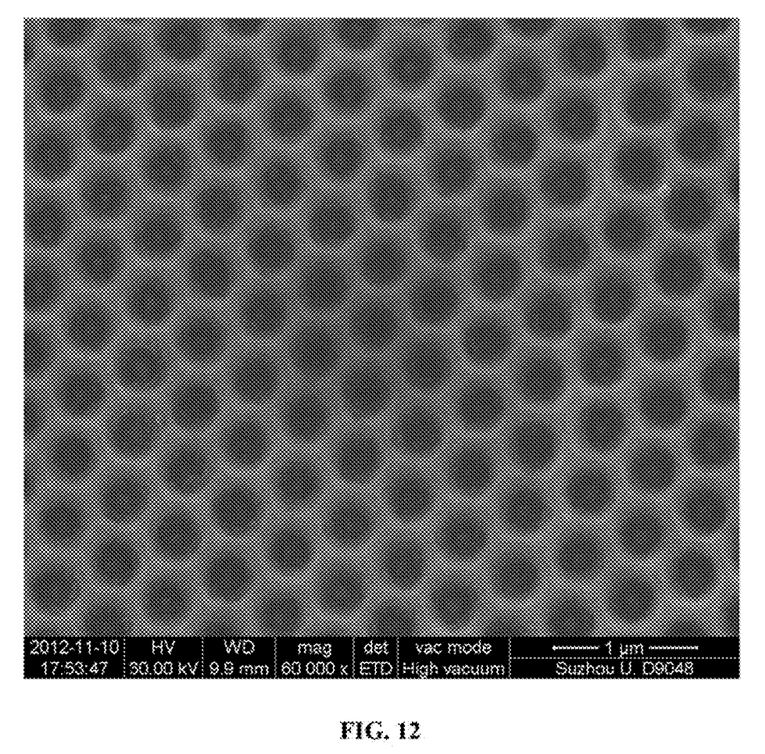
FIG. 12 is a morphology from the SEM of a three-layer metal oxide porous film, prepared in Example 2, which is similar to that of the multilayer metal oxide porous film prepared in Example 1.
Figure 13:
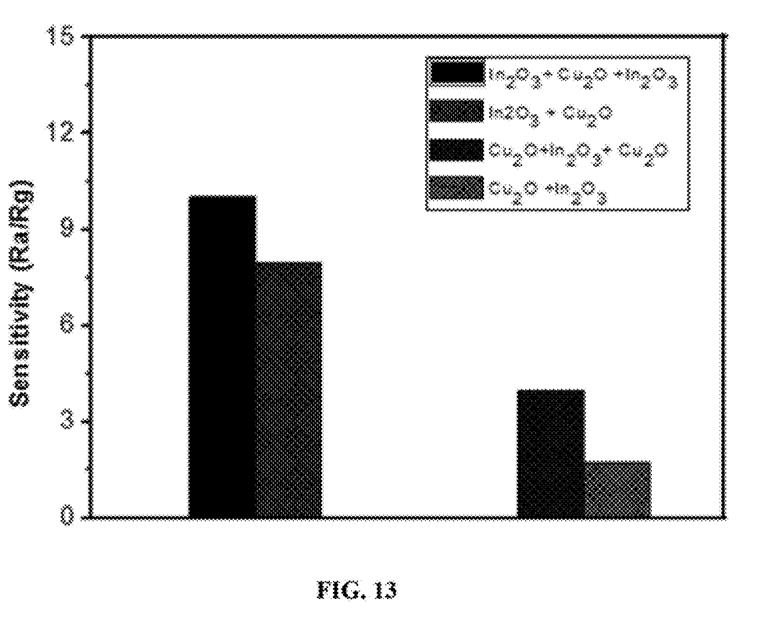
FIG. 13 is a comparison diagram of sensitivity of different multilayer metal oxide porous films prepared in Example 2 with respect to ethanol of 1000 ppm at the temperature of 150° C.

The morphology of the metal oxide porous film gas sensitive material pared by using this method is shown in FIG. 13, and it can be seen from FIG. 12 that the morphology of the prepared multilayer metal oxide porous film gas sensitive material is similar to the morphology of the metal oxide porous film prepared by using the method in Example 1. The comparison diagram of the gas sensitive responses of the double-layer metal oxide porous film gas sensitive material and the three-layer metal oxide porous film prepared by using this method is shown in FIG. 13, and it can be seen from FIG. 13 that, the gas sensitive response of the three-layer metal oxide porous film gas sensitive material is higher than the gas sensitive response of the double-layer metal oxide porous film.

What is claimed is:

1. A method for preparing a multilayer metal oxide nano-porous film gas sensitive material, comprising the following steps:
   Step 1-self-assembling the polystyrene microsphere single-layer template on a Si substrate covered with $SiO_2$ by using a solution evaporation method;
   Step 2-etching the polystyrene microsphere template by using a reactive ion etching method, to reduce the pitches between PSs;
   Step 3-depositing, on the substrate processed in Step 2, 40 nm $Cu_2O$+40 nm $In_2O_3$ with indium oxide being in the bottom layer, and cuprous oxide being in the top layer, 40 nm $In_2O_3$+40 nm $Cu_2O$ with cuprous oxide being in the bottom layer, and indium oxide being in the top layer, 30 nm $Cu_2O$+20 nm $In_2O_3$, +30 nm $Cu_2O$ with indium oxide being in the intermediate layer, and 30 nm $In_2$ $O_3$+20 nm $Cu_2O$+30 nm $In_2O_3$ with cuprous oxide being in the intermediate layer, using a magnetron sputter physical deposition method; and
   Step 4-placing the processed substrate of step 3 in toluene for ultrasonic treatment to remove the polystyrene microsphere template, and performing annealing for 4 h in air atmosphere at the temperature of 550° C.

2. The method for preparing a multilayer metal oxide nano-porous film gas sensitive material according to claim 1, wherein the thickness of $SiO_2$ in Step 1 is between 100 nm and 10 μm.

3. The method for preparing a multilayer metal oxide nano-porous film gas sensitive material according to claim 1, wherein in Step 2, the flow rate of the fed plasma gas $O_2$ is controlled to be 40 sccm, the pressure in the reaction cavity is controlled to be 37 mTorr, the power applied to excite the $O_2$ plasma is controlled to be 90 W, and the $O_2$ plasma etching time is controlled to be 1 min.

4. The method for preparing a multilayer metal oxide nano-porous film gas sensitive material according to claim 1, wherein in Step 3, the target material used for magnetron sputtering is a ceramics target material of indium oxide or cuprous oxide, the power for exciting the Ar plasma is 80 W, and the pressure in the cavity is 3 mTorr.

* * * * *